(12) United States Patent
Dupuis

(10) Patent No.: US 6,258,367 B1
(45) Date of Patent: Jul. 10, 2001

(54) COSMETIC COMPOSITION COMPRISING AT LEAST ONE NONIONIC AMPHIPHILIC ASSOCIATIVE POLYURETHANE AND AT LEAST ONE QUATERNARY SILICONE

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/402,797

(22) PCT Filed: Dec. 23, 1998

(86) PCT No.: PCT/FR98/02865

§ 371 Date: Dec. 22, 1999

§ 102(e) Date: Dec. 22, 1999

(87) PCT Pub. No.: WO99/40892

PCT Pub. Date: Aug. 19, 1999

(30) Foreign Application Priority Data

Feb. 13, 1998 (FR) .................................................. 98 01776

(51) Int. Cl.⁷ ............................... A61K 7/00; A61K 7/06
(52) U.S. Cl. ....................... 424/401; 424/70.1; 424/401
(58) Field of Search .................................. 424/400, 401, 424/70.1

(56) References Cited

U.S. PATENT DOCUMENTS

| | | | |
|---|---|---|---|
| 4,833,225 | 5/1989 | Schaefer et al. | 528/28 |
| 4,891,166 | 1/1990 | Schaefer et al. | 556/418 |
| 5,294,692 | 3/1994 | Barron et al. | 526/301 |
| 5,344,643 | 9/1994 | Thiel et al. | 424/70.1 |
| 5,478,562 | 12/1995 | Cauwet et al. | 424/401 |
| 5,538,717 | 7/1996 | La Poterie | 424/61 |
| 5,661,118 | 8/1997 | Cauwet et al. | 510/126 |

FOREIGN PATENT DOCUMENTS

| | | |
|---|---|---|
| 37 05 121 | 9/1988 | (DE) . |
| 37 19 086 | 10/1988 | (DE) . |
| 44 38 846 | 5/1996 | (DE) . |
| 0 282 720 | 9/1988 | (EP) . |
| 0 339 712 | 11/1989 | (EP) . |
| 0 412 705 | 2/1991 | (EP) . |
| 0 415 705 | 3/1991 | (EP) . |
| 0 530 974 | 3/1993 | (EP) . |
| 0 555 155 | 8/1993 | (EP) . |
| 0 617 607 | 10/1994 | (EP) . |
| 0 637 600 | 2/1995 | (EP) . |
| 0 648 485 | 4/1995 | (EP) . |
| 0 714 654 | 6/1996 | (EP) . |
| 0 745 373 | 12/1996 | (EP) . |
| 0 824 914 | 2/1998 | (EP) . |
| 2 733 910 | 11/1996 | (FR) . |
| 2 738 835 | 3/1997 | (FR) . |
| 2 750 047 | 12/1997 | (FR) . |
| 2 758 262 | 7/1998 | (FR) . |

OTHER PUBLICATIONS

English language Derwent Abstract of DE 37 05 121. 9/88.
English language Derwent Abstract of DE 44 38 846. 10/88.
English language Derwent Abstract of EP 0 637 600. 2/95.
English language Derwent Abstract of EP 0 714 654. 6/96.
English language Derwent Abstract of EP 0 745 373. 12/96.
English language Derwent Abstract of FR 2 738 835. 3/97.
English language Derwent Abstract of FR 2 733 910. 11/96.
English language Derwent Abstract of FR 2 750 047. 12/97.
English language Derwent Abstract of FR 2 758 262. 7/98.

*Primary Examiner*—Shelley A. Dodson
(74) *Attorney, Agent, or Firm*—Finnegan, Henderson, Farabow, Garrett & Dunner, L.L.P.

(57) ABSTRACT

A cosmetic composition having, in a cosmetically acceptable medium, at least one nonionic amphiphilic associative polyurethane, and at least one silicone containing quaternary ammonium groups.

21 Claims, No Drawings

COSMETIC COMPOSITION COMPRISING AT LEAST ONE NONIONIC AMPHIPHILIC ASSOCIATIVE POLYURETHANE AND AT LEAST ONE QUATERNARY SILICONE

This application is a 371 of PCT/FR98/02865 filed Dec. 23, 1998.

The present invention relates to cosmetic compositions containing a novel thickening system based on associative polyurethanes, as well as to their use in particular as leave-in haircare gels or styling gels.

The thickening and/or gelation of aqueous media with polymers has been an important subject of cosmetic research for a long time. The production of an advantageous thickening effect with a water-soluble polymer generally assumes a high molar mass and a large hydrodynamic volume. The gelation of an aqueous medium is then considered as being the result of a three-dimensional polymer network obtained by crosslinking linear polymers or by copolymerizing bifunctional and polyfunctional monomers. However, the use of such polymers of very high molar mass poses a certain number of problems, such as the relatively unpleasant texture and the difficulty in spreading the gels obtained.

One advantageous approach consists in using, as thickeners, polymers capable of reversibly self-associating or of associating with other molecules or particles. This physical association gives rise to thixotropic or rheofluidizing macromolecular systems, i.e. systems whose viscosity depends on the shear forces to which they are subjected.

Such polymers capable of reversibly self-associating or of associating with other molecules are known as "associative polymers". The forces of interaction in play can be very different in nature, for example of electrostatic nature, of hydrogen bonding type or hydrophobic interactions.

One specific case of associative polymers is amphiphilic polymers, i.e. polymers comprising one or more hydrophilic portions which make them soluble in water, and one or more hydrophobic zones via which the polymers interact and self-asserble or assemble with other molecules.

It is known practice to prepare hair compositions in gel form using, as thickening system, such associative amphiphilic polymers, in combination with surfactants. It is thought that the advantageous rheological properties of the gels thus obtained result from the formation of mixed micelles formed by the surfactants and by the hydrophobic portions of the amphiphilic polymers, these micelles constituting a multitude of physical crosslinking points.

However, these compositions based on associative polymers and surfactants do not always have the desired cosmetic properties. Thus, the presence of surfactants, even in small amounts, can bring about an undesirable change in the cosmetic properties of the said compositions, such as the properties of application or of feel after drying. Moreover, in particular in the sector of leave-in haircare or styling gels, it is important to be able to distribute the product uniformly over the entire head of hair so as to avoid excessive loads and the cosmetic defects resulting therefrom.

French patent application No. 2,738,835 relates to aqueous cosmetic compositions thickened using at least one amphiphilic polymer associated with at least one protein containing a hydrophobic group.

It has now been discovered that it is possible to obtain a good thickening, or even gelling, effect and advantageous cosmetic properties by combining associative amphiphilic polyurethanes with silicones containing quaternary ammonium groups.

The gel obtained by this combination has a very melting texture and is pleasant to apply. The final feel on dried hair is more pleasant and less laden. The gel moreover has excellent styling power.

One subject of the present invention is thus a cosmetic composition comprising at least one associative nonionic polyurethane in combination with at least one silicone containing quaternary ammonium groups.

Another subject of the present invention is the use of the combination of at least associative nonionic polyurethane and at least one silicone containing quaternary ammonium groups as a thickening system, in particular for the manufacture of leave-in haircare and styling gels.

A third subject of the invention is a cosmetic process for treating the hair with cosmetic compositions comprising at least one nonionic associative polyurethane and at least one silicone containing quaternary ammonium groups.

Other subjects will become apparent on reading the description and the examples which follow.

The cosmetic compositions in accordance with the invention are essentially characterized in that they contain, in a cosmetically acceptable medium, (A) at least one amphiphilic nonionic associative polyurethane, and (B) at least one silicone containing quaternary ammonium groups.

The nonionic associative polyurethanes used in the present invention preferably correspond to the general formula

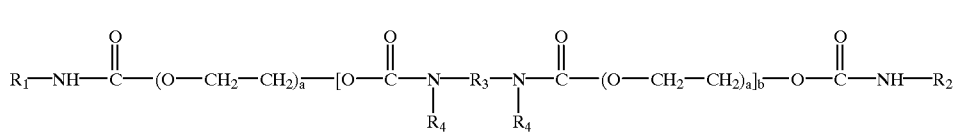

(I)

in which
at least one of the radicals $R_1$ and $R_2$ represents a $C_8$–$C_{18}$ higher alkyl group and the other, where appropriate, represents a $C_1$–$C_6$ lower alkyl group, preferably a $C_1$–$C_4$ lower alkyl group,
$R_3$ represents a $C_4$–$C_{36}$, preferably $C_6$–$C_{10}$, hydrocarbon-based radical,
$R_4$ represents a hydrogen atom or a $C_1$–$C_6$ alkyl radical, preferably a hydrogen atom,
a ranges, independently, from 90 to 600, and
b is from 1 to 4.

According to the invention, the expression "$C_1$–$C_5$ lower alkyl group" means an alkyl group containing a linear or branched chain comprising from 1 to 6 carbon atoms, such as methyl, ethyl, n-propyl, n-butyl, n-pentyl and n-hexyl radicals, as well as the corresponding branched isomers.

In accordance with the invention, the $C_8$–$C_{18}$ higher alkyl groups denote alkyl groups containing a linear or branched chain comprising from 8 to 18 carbon atoms, such as octyl, nonyl, decyl, undecyl, dodecyl, tridecyl, tetradecyl, pentadecyl, hexadecyl, heptadecyl and octadecyl radicals.

In one preferred embodiment, only one of the radicals $R_1$ and $R_2$ represents a $C_8$–$C_{18}$ higher alkyl chain and the other represents a $C_1$–$C_6$ lower alkyl group.

An associative polyurethane in which one of the radicals in α, ω represents an octadecyl group and the other represents a methyl group is used in particular.

The associative polyurethanes used in the compositions of the present invention are used in the form of an aqueous solution or suspension optionally containing a certain amount of soluble starch. This starch can be any starch extracted from natural sources, such as wheat starch, cornstarch, rice starch, potato starch, etc. and which has been chemically, enzymatically or microbiologically modified so as to be soluble in water.

A preferred polymer is sold by the company Rohm & Haas under the name Acrysol 46. It is a polyurethane obtained by condensation of hexamethylene diisocyanate and polyethylene glycol, and bearing, on average, a methyl residue and an octadecyl residue at its ends, respectively. This polymer is in the form of an aqueous solution containing 15% by weight of polyurethane active material also containing 3–5% of an enzymatically modified starch matrix.

In accordance with the invention, the expression "silicone containing quaternary ammonium groups" means any silicone comprising one or more quaternary ammonium groups. These quaternary ammonium groups can be attached in the α-ω positions or in the form of side groups. They can be attached directly to the polysiloxane skeleton or can be borne by hydrocarbon-based chains, in particular polyoxyalkylene chains.

According to the invention, in accordance with the generally accepted meaning, the term "silicone" means any polymer having a structure based on the alternation of silicon and oxygen atoms, linked together via so-called siloxane (—Si—O—Si—) bonds, and also characterized by the existence of silicon-carbon bonds. These silicones, or polysiloxanes, are generally obtained by polycondensation of suitably functionalized silanes. The hydrocarbon-based radicals most commonly borne by the silicon atoms are lower alkyl radicals, in particular methyl, fluoroalkyl radicals, aryl radicals and in particular phenyl.

The silicones containing quaternary ammonium groups of the present invention are chosen, for example, from the compounds corresponding to the following general formulae:

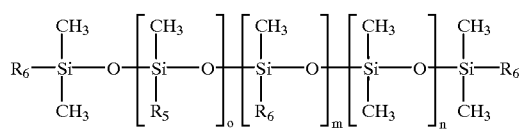

(II)

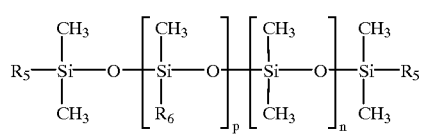

(III)

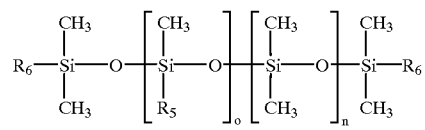

(IV)

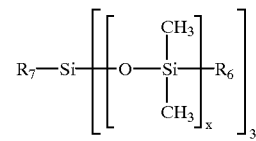

(V)

in which formulae:

the radicals $R_5$, which may be identical or different, represent linear or branched $C_1$–$C_{30}$ alkyl radicals, or phenyl radicals;

the radicals $R_6$, which may be identical or different, represent a group —$C_eH_{2e}$—O—$(C_2H_4O)_c$—$(C_3H_6O)_d$—$R_8$ or —$C_eH_{2e}$—O—$(C_4H_8O)_c$—$R_8$, the radicals $R_7$, which may be identical or different, denote a linear or branched $C_1$–$C_{12}$ alkyl radical and preferably a methyl radical;

the radicals $R_8$, which may be identical or different, represent a group

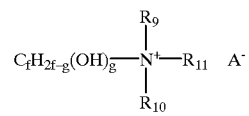

the radicals $R_{11}$ represent, independently, a linear or branched $C_1$–$C_{22}$ alkyl or $C_2$–$C_{22}$ alkenyl radical, optionally bearing one or more OH groups, or represent a group $C_hH_{2h}Z_iCOR_{12}$;

$R_9$, $R_{10}$ and $R_{12}$, which may be identical or different, represent linear or branched $C_1$–$C_{22}$ alkyl or $C_2$–$C_{22}$ alkenyl radicals, optionally bearing one or more OH groups, or $R_{10}$ can form, with a portion of $R_{11}$, an imidazoline ring, c ranges from 0 to 50, d ranges from 0 to 50, e and f range, independently, from 0 to 4, m ranges from 0 to 20, n ranges from 0 to 500, o ranges from 0 to 20, p ranges from 1 to 50, x ranges from 1 to 100, g ranges from 0 to 2, h ranges from 1 to 4, Z represents an oxygen or nitrogen atom, i is 0 or 1, and $A^-$ represents a halide ion or an organic anion of carboxylate, phosphate, alkanesulphate or sulphate type.

Such silicones are sold, for example, by the company Goldschmidt under the names Abil Quat 3272, Abil B 9905, Abil Quat 3474 and Abil K 3270, by the company Lipo France under the names Silquat Q-100, Biosil Basics Cetylsil, Silquat Q-200 WS, Silquat AX, Silquat AC, Silquat AD and Silquat AM, all manufactured by the company Siltech, by the company OSI under the name Magnasoft Exhaust and Silsoft C-880, and by the company UCIB under the names Pecosil 14-PQ and Pecosil 36-PQ (manufactured by Phoenix Chemical).

These silicones are described in particular in patents EP 530,974, DE 3,719,086, DE 3,705,121, EP 617,607 and EP 714,654.

Silicones containing quaternary ammonium groups which are used in accordance with the invention can be in the form of aqueous solutions or optionally in the form of dispersions or emulsions in water.

The silicones containing quaternary ammonium groups and the associative polyurethanes are used in amounts which are sufficient to obtain a satisfactory thickening or gelation of the aqueous medium.

An amount of associative polyurethanes of between 0.1 and 10% by weight, and preferably between 0.5 and 5% by weight, in terms of active material relative to the total weight of the composition, is used in particular.

In the compositions of the present invention, the silicone (s) containing quaternary ammonium groups is (are) present in a proportion of from 0.01 to 10% by weight, preferably in a proportion of from 0.1 to 5% by weight, of active material relative to the total weight of the composition.

The silicones are preferably used in an amount such that the silicone/amphiphilic polyurethane weight ratio is between 0.1 and 10.

The cosmetically acceptable medium preferably consists of water and can also contain cosmetically acceptable solvents, for example lower monoalcohols such as ethanol or isopropanol, glycols such as ethylene glycol, glycol ethers such as the alkyl ethers of ethylene glycol or of diethylene glycol, or alternatively fatty acid esters, all of these solvents being used alone or in the form of a mixture.

The haircare or styling gels can also contain one or more additives usually used in such hair compositions. Mention may be made, for example, of fragrances, dyes, preserving agents, sunscreens, vitamins, pH regulators, etc. It is clearly understood that the choice of these compounds should take into account possible interactions with the thickening system. A person skilled in the art will take care to ensure that the addition of these additives will not have an unfavourable influence on the advantageous properties of the compositions obtained by means of the present invention.

One preferred cosmetic process for treating the hair, according to the invention, consists in applying and homogeneously distributing the compositions defined above on the hair and in drying the hair thus treated without rinsing it.

It is clearly understood that the description hereinabove has been given purely for illustrative purposes and without any limitation being implied, and that variations or modifications may be made thereto in the context of the present invention.

The examples which follow are intended to illustrate the invention without thereby being limiting in nature.

EXAMPLE 1

The aqueous compositions below are prepared, comprising 2% by weight of associatve polyurethane active material and 1% of silicone active material containing quaternary ammonium groups or of cationic silicones.

| Associative polyurethane | silicone | nature of the silicone | consistency of the composition obtained |
|---|---|---|---|
| Acrysol 46 | Abil Quat 3272 | quaternized | gel |
| Acrysol 46 | Silquat Q-100 | quaternized | gel |
| Acrysol 46 | Biosil Basic Cetylsil | quaternized | gel |
| Acrysol 46 | SLM 23056/1 | non-quaternized | fluid solution |
| Acrysol 46 | Finish CT 110E | non-quaternized | fluid solution |
| Acrysol 46 | none | — | fluid solution |

The silicones used are as follows:

Abil Quat 3272 is a polydimethylsiloxane containing quaternary ammonium acetate groups containing $\alpha$ and $\omega$ coconut fatty chains (50% solution in propylene glycol) sold by the company Goldschmidt;

Silquat Q-100 is a polydimethylsiloxane containing propyloxy-hydroxy-2-propyltrimethylammonium chloride groups (alcoholic 70% solution) sold by the company Lipo France;

Biosil Basic Cetylsil is an oxyethylenated polydimethylsiloxane containing phthalic ester/ cetyltriethylammonium chloride groups (aqueous 40% solution) sold by the company Siltech;

Finish CT110 E is a polydimethyl/ methylcyclohexylaminopropyl siloxane (as a nonionic amulsion) sold by the company Wacker; and SLM 23 056/1 is a polydimethylsiloxane containing aminoethylaminopropyl and $\alpha$, $\omega$ lauryl groups, sold by the company Wacker.

It is found that the combination of preferred amphiphilic polyurethane of the present invention (Acrysol 46) and of a non-quaternized silicone does not allow gelation of the aqueous medium, but instead gives rise to a fluid solution whose viscosity is little different from that of a polyurethane solution alone. On the other hand, the addition of only 1% by weight of one of the silicones containing quaternary ammonium groups of the present invention to a polyurethane solution is reflected by satisfactory gelation of this same aqueous medium.

EXAMPLE 2

A care gel having the composition below was prepared:

| Acrysal 46 | 2.5% active material |
|---|---|
| Abil Quat 3272 | 1.5% active material | fragrance, dye, preserving agent demineralized water q.s. 100 g

EXAMPLE 3

A care gel having the composition below was prepared:

| Acrysol 46 | 3% active material |
|---|---|
| Sil Quat Q100 | 2% active material | fragrance, dye, preserving agent demineralized water q.s. 100 g

What is claimed is:

1. A cosmetic composition comprising, in a cosmetically acceptable medium,
   (A) at least one nonionic amphiphilic associative polyurethane, and
   (B) at least one silicone containing quaternary ammonium groups.

2. A cosmetic composition according to claim 1, wherein the at least one nonionic amphiphilic associative polyurethane has the formula (I):

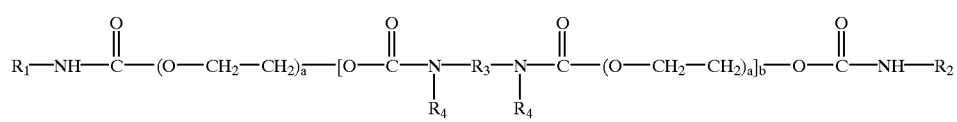

in which
   at least one of the radicals $R_1$ and $R_2$ is a higher alkyl group having 8 to 18 carbons,
   $R_3$ is a hydrocarbon-based radical having from 4 to 36 carbons,
   $R_4$ is chosen from a hydrogen atom and $C_1$–$C_6$ alkyl radicals,
   a ranges, independently, from 90 to 600, and
   b ranges from 1 to 4.

3. The composition according to claim 2, wherein $R_3$ has from 6 to 10 carbons.

4. The composition according to claim 2, wherein $R_4$ is a hydrogen atom.

5. The composition according to claim 2, wherein one of the groups $R_1$ and $R_2$ is a $C_8$–$C_{18}$ higher alkyl group and the other group is a $C_1$–$C_6$ lower alkyl group.

6. The composition according to claim 5, wherein the lower alkyl group has 1 to 4 carbons.

7. The composition according to claim 6, wherein the higher alkyl group is an octadecyl group and the lower alkyl group is a methyl group.

8. The composition according to claim 7, wherein the at least one nonionic amphiphilic associative polyurethane of formula (I) is obtained by polycondensation of hexamethylene diisocyanate and polyethylene glycol.

9. The composition according to claim 2, wherein the at least one nonionic amphiphilic associative polyurethane of formula (I) is in a solution or suspension in water, which also contains chemically, enzymatically or microbiologically modified soluble starch.

10. The composition according to claim 1, wherein the at least one silicone containing quaternary ammonium groups is chosen from a silicone corresponding to one of the following formulae:

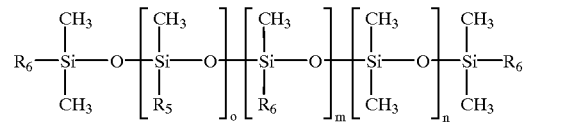

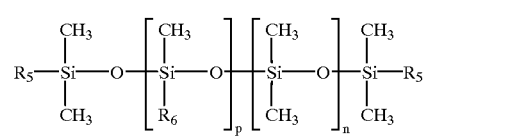

-continued

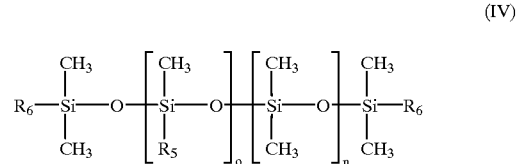

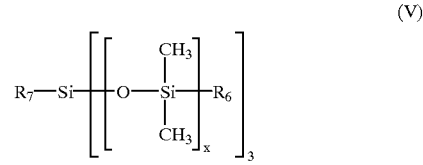

in which formulae:
   the $R_5$ radicals, which may be identical or different, are chosen from or phenyl radicals and linear and branched $C_1$–$C_{30}$ alkyl radicals;
   the $R_6$ radicals, which may be identical or different, are chosen from —$C_eH_{2e}$—O—$(C_2H_4O)_c$—$(C_3H_6O)_d$—$R_8$ and —$C_eH_{2e}$—O—$(C_4H_8O)_c$—$R_8$,
   the $R_7$ radical is chosen from linear and branched $C_1$–$C_{12}$ alkyl radicals;
   the $R_8$ radicals, which may be identical or different, are a

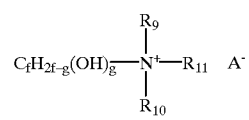

the $R_{11}$ radicals are, independently, chosen from a $C_hH_{2h}Z_jCOR_{12}$ group, and linear or branched $C_1$–$C_{22}$ alkyl and $C_2$–$C_{22}$ alkenyl radicals, optionally bearing one or more OH groups, the $R_9$, $R_{10}$ and $R_{12}$ radicals, which may be identical or different, are chosen from linear and branched $C_1$–$C_{22}$ alkyl and $C_2$–$C_{22}$ alkenyl radicals, optionally bearing one or more OH groups, or $R_{10}$ can form, with a portion of $R_{11}$, an imidazoline ring, c ranges from 0 to 50, d ranges from 0 to 50, e and f range, independently, from 0 to 4, m ranges from 0 to 20, n ranges from 0 to 500, o ranges from 0 to 20, p ranges from 1 to 50, x ranges from 1 to 100, g ranges from 0 to 2, h ranges from 1 to 4, Z is chosen from oxygen and nitrogen, i is 0 or 1, and $A^-$ is chosen from halide ions and organic carboxylate, phosphate, alkanesulphate, and sulphate anions.

11. The composition according to claim 10, wherein $R_7$ radical is a methyl radical.

12. The composition according to claim 1, wherein the at least one silicone containing quaternary ammonium groups is in a solution, suspension or dispersion in water.

13. The composition according to claim 10, wherein the at least one silicone containing quaternary ammonium groups is chosen from polydimethylsiloxanes containing quaternary ammonium acetate groups containing α and ω coconut fatty chains, polydimethylsiloxanes containing propyloxy-hydroxy-2-propyltrimethylammonuium chloride groups, and oxyethylenated polydimethylsiloxanes containing phthalic ester/cetyltriethylammonium chloride groups.

14. The composition according to claim 1, wherein the at least one nonionic amphiphilic associative polyurethane of formula (I) is present in an amount of from 0.1 to 10% by weight of active material relative to the total weight of the composition.

15. The composition according to claim 14, wherein the at least one nonionic amphiphilic associative polyurethane of formula (I) is present in an amount of from 0.5 to 5% by weight of active material relative to the total weight of the composition.

16. The composition according to claim 1, wherein the at least one silicone containing quaternary ammonium groups is present in an amount of from 0.01 to 10% by weight of active material relative to the total weight of the composition.

17. The composition according to claim 16, wherein the at least one silicone containing quaternary ammonium groups is present in an amount of from 0.1 to 5% by weight of active material relative to the total weight of the composition.

18. The composition according to claim 1, wherein the weight ratio of the at least one silicone containing quaternary ammonium groups and the at least one nonionic amphiphilic polyurethane ranges from about 0.1 to 10.

19. A leave-in haircare gel or styling gel comprising, in a cosmetically acceptable medium:

(A) at least one nonionic amphiphilic associative polyurethane, and (B) at least one silicone containing quaternary ammonium groups.

20. A process of thickening a cosmetic composition comprising adding at least one nonionic amphiphilic associative polyurethane and at least one silicone containing quaternary ammonium groups to the composition in an amount effective to thicken said composition.

21. A process for treating hair comprising applying a composition comprising, in a cosmetically acceptable medium:

(A) at least one nonionic associative polyurethane, and (B) at least one silicone containing quaternary ammonium groups to the hair and drying the hair without rinsing said composition from the hair.

* * * * *

UNITED STATES PATENT AND TRADEMARK OFFICE
CERTIFICATE OF CORRECTION

PATENT NO. : 6,258,367 B1  Page 1 of 1
DATED : July 10, 2001
INVENTOR(S) : Dupuis It is certified that error appears in the above-identified patent and that said Letters Patent is hereby corrected as shown below:

<u>Column 8, claim 10,</u>
Line 56, insert -- group -- after "are a"

Signed and Sealed this

Second Day of April, 2002

Attest:

JAMES E. ROGAN
*Attesting Officer*  *Director of the United States Patent and Trademark Office*